(12) United States Patent
Mansfield et al.

(10) Patent No.: US 11,344,324 B2
(45) Date of Patent: May 31, 2022

(54) SURGICAL TOOL FOR OPERATING A SHEATH AND A WIRE

(71) Applicant: Gyrus ACMI, Inc., Southborough, MA (US)

(72) Inventors: Richard P. Mansfield, Sterling, MA (US); Judy L. Walish, West Roxbury, MA (US); Stephen P. Femia, Holden, MA (US)

(73) Assignee: Gyrus Acmi, Inc., Westborough, MA (US)

( * ) Notice: Subject to any disclaimer, the term of this patent is extended or adjusted under 35 U.S.C. 154(b) by 400 days.

(21) Appl. No.: 16/082,344

(22) PCT Filed: Mar. 10, 2016

(86) PCT No.: PCT/IB2016/051381
§ 371 (c)(1),
(2) Date: Sep. 5, 2018

(87) PCT Pub. No.: WO2017/153810
PCT Pub. Date: Sep. 14, 2017

(65) Prior Publication Data
US 2019/0083116 A1    Mar. 21, 2019

(51) Int. Cl.
*A61B 17/221* (2006.01)
*A61B 1/307* (2006.01)
*A61B 17/00* (2006.01)

(52) U.S. Cl.
CPC ............ *A61B 17/221* (2013.01); *A61B 1/307* (2013.01); *A61B 17/00234* (2013.01);
(Continued)

(58) Field of Classification Search
CPC ........ A61B 17/221; A61B 2017/00358; A61B 2017/2212; A61B 2017/2215; A61B 2017/2217
See application file for complete search history.

(56) References Cited

U.S. PATENT DOCUMENTS

| | | | |
|---|---|---|---|
| 5,147,303 A | 9/1992 | Martin | 604/110 |
| 5,403,324 A | 4/1995 | Ciervo et al. | 606/128 |

(Continued)

FOREIGN PATENT DOCUMENTS

| | | |
|---|---|---|
| CN | 103142260 A | 6/2013 |
| CN | 104837421 A | 8/2015 |

(Continued)

OTHER PUBLICATIONS

"Chinese Application Serial No. 201680081233.6, Office Action dated Nov. 4, 2020", with English translation, 16 pgs.

(Continued)

*Primary Examiner* — Martin T Ton
(74) *Attorney, Agent, or Firm* — Schwegman Lundberg & Woessner, P.A.

(57) ABSTRACT

A tool for use by a surgeon for coupling to a working channel port and for operating a sheath and wire including a basket device for capturing an object to be removed from a body. The tool includes a controller adapted to be coupled to the sheath and the wire for selectively controlling the position of the wire with respect to the sheath and for operating the basket device between a first, closed position and a second, open position, the controller including a base portion having a wire actuation unit including a movable plunger for coupling with the wire and for moving the wire with respect to the sheath; and a sheath control unit removably coupled to the wire actuation unit for independently controlling the position of the sheath. The controller is configured to longitudinally move the wire and operate the basket device to selectively open and close the basket.

18 Claims, 7 Drawing Sheets

(52) U.S. Cl.
CPC ............... *A61B 2017/0046* (2013.01); *A61B 2017/00358* (2013.01); *A61B 2017/00367* (2013.01); *A61B 2017/2212* (2013.01)

(56) References Cited

U.S. PATENT DOCUMENTS

| | | | |
|---|---|---|---|
| 5,720,754 | A | 2/1998 | Middleman et al. ......... 606/127 |
| 6,764,499 | B2 | 7/2004 | Honey et al. ................. 606/207 |
| 7,744,583 | B2 | 6/2010 | Seifert et al. ................ 604/507 |
| 8,211,115 | B2 | 7/2012 | Cheng et al. ................ 606/114 |
| 8,608,690 | B2 | 12/2013 | Pal ........................... 604/103.04 |
| 2002/0091394 | A1 | 7/2002 | Reynolds et al. ............ 606/127 |
| 2004/0015050 | A1* | 1/2004 | Goto .................. A61B 18/1492 600/104 |
| 2004/0049095 | A1 | 3/2004 | Goto et al. |
| 2004/0199200 | A1 | 10/2004 | Teague et al. ............... 606/200 |
| 2005/0192592 | A1 | 9/2005 | Butler et al. ................. 606/114 |
| 2007/0198002 | A1* | 8/2007 | Melsheimer ..... A61B 17/32056 606/1 |
| 2008/0167527 | A1* | 7/2008 | Slenker .............. A61B 1/00135 600/156 |
| 2008/0188890 | A1 | 8/2008 | Weitzner ..................... 606/205 |
| 2012/0095477 | A1 | 4/2012 | Bilitz ........................... 606/127 |
| 2013/0035695 | A1 | 2/2013 | Uihlein et al. |
| 2013/0211415 | A1 | 8/2013 | Zerfas et al. ................ 606/114 |
| 2014/0249540 | A1* | 9/2014 | Nieman .............. A61B 17/221 606/113 |
| 2014/0257253 | A1* | 9/2014 | Jemison .......... A61B 17/32056 606/1 |
| 2014/0316203 | A1* | 10/2014 | Carroux ............ A61B 1/00133 600/146 |
| 2016/0135795 | A1* | 5/2016 | Eto .................... A61B 17/3478 600/566 |
| 2017/0056033 | A1* | 3/2017 | Okada ................. A61B 17/221 |
| 2019/0069915 | A1* | 3/2019 | Mansfield .......... A61B 1/00133 |

FOREIGN PATENT DOCUMENTS

| | | |
|---|---|---|
| CN | 104956198 A | 9/2015 |
| CN | 105392415 A | 3/2016 |
| CN | 108601601 A | 9/2018 |
| GB | 809773 | 10/1956 |
| JP | 2004057814 A | 2/2004 |
| JP | 2006502760 A | 1/2006 |
| JP | 2019509108 A | 4/2019 |
| JP | 6714713 B2 | 6/2020 |
| WO | WO-2004/014242 A1 | 2/2004 |
| WO | WO 2004/069059 A2 | 8/2004 |
| WO | WO-2014174378 A1 | 10/2014 |
| WO | WO-2017153810 A1 | 9/2017 |

OTHER PUBLICATIONS

"International Application Serial No. PCT/IB2016/051381, International Preliminary Report on Patentability dated Sep. 20, 2018", 11 pgs.

"International Application Serial No. PCT/IB2016/051381, International Search Report dated Jul. 13, 2016", 6 pgs.

"International Application Serial No. PCT/IB2016/051381, Written Opinion dated Jul. 13, 2016", 9 pgs.

"Japanese Application Serial No. 2018-545619, Notice of Reasons for Refusal dated Nov. 18, 2019", w/ English Translation, 27 pgs.

"Japanese Application Serial No. 2018-545619, Response filed Mar. 17, 2020 to Notice of Reasons for Refusal dated Nov. 18, 2019", w/ English Translation, 25 pgs.

"Chinese Application Serial No. 201680081233.6, Office Action dated Jul. 1, 2021", w/English Translation, 17 pgs.

"Chinese Application Serial No. 201680081233.6, Response filed Mar. 17, 2021 to Office Action dated Nov. 4, 2020", w/English Claims, 21 pgs.

"Chinese Application Serial No. 201680081233.6, Response filed Sep. 13, 2021 to Office Action dated Jul. 1, 2021", w English Claims, 14 pgs.

\* cited by examiner

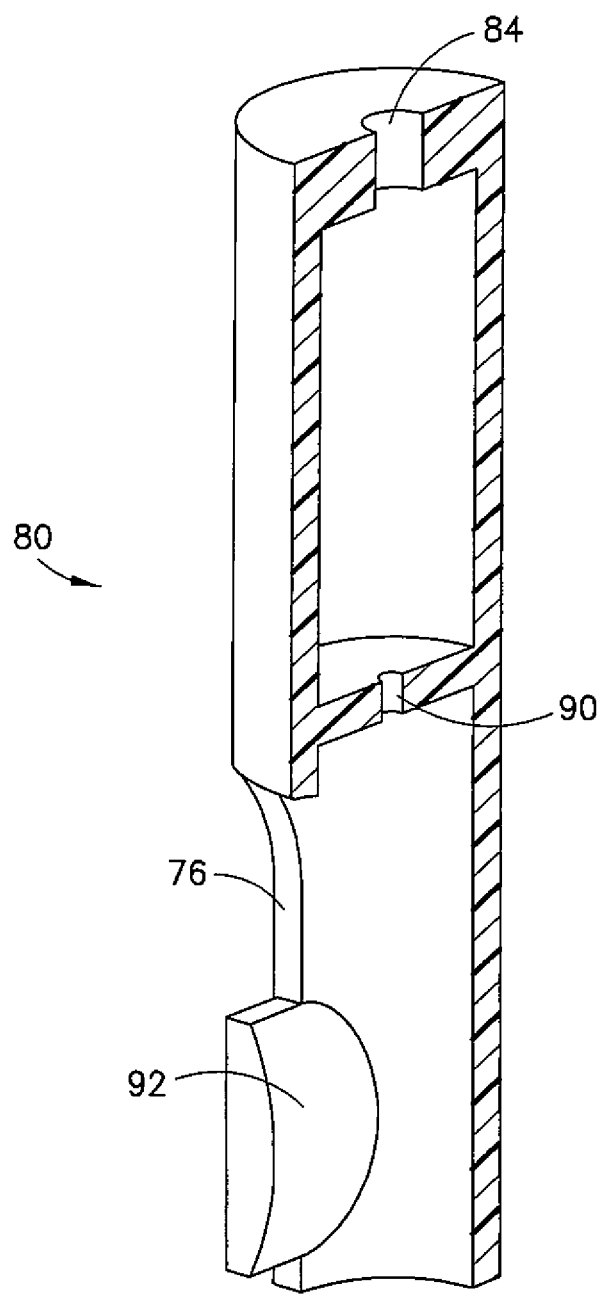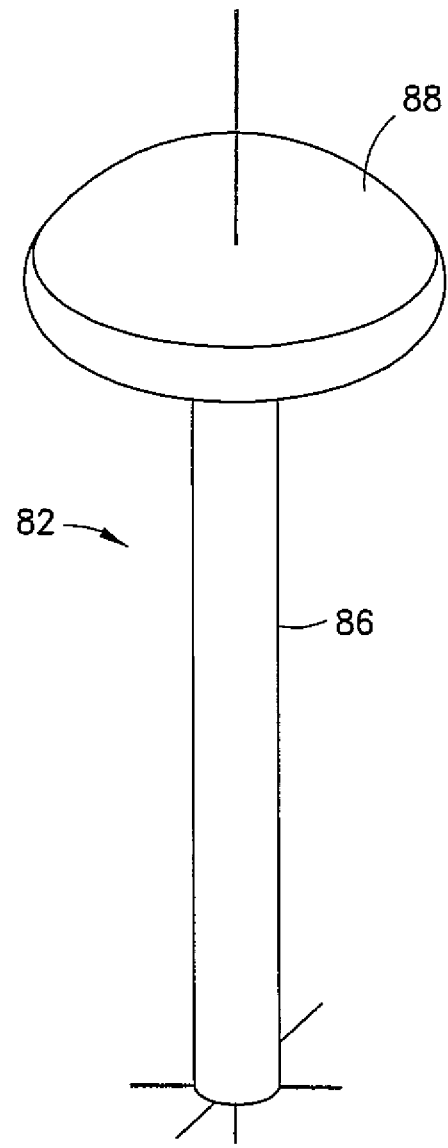
FIG.7
FIG.8

SURGICAL TOOL FOR OPERATING A SHEATH AND A WIRE

This patent application is a U.S. National Stage application of International Patent Application Number PCT/IB2016/051381 filed Mar. 10, 2016, which is hereby incorporated by reference in its entirety.

BACKGROUND

Technical Field

The exemplary and non-limiting embodiments relate generally to an endoscope and, more particularly, to an apparatus used with an endoscope.

Brief Description of Prior Developments

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, an example embodiment is provided in a tool for use by a surgeon, the tool for coupling to a luer port and for operating a sheath and wire including a basket device for capturing an object to be removed from a body of an animal, the tool comprising: a controller adapted to be coupled to the sheath and the wire for selectively controlling the position of the wire with respect to the sheath and for operating the basket device between a first, closed position and a second, open position, the controller including a base portion comprising: a wire actuation unit including a movable plunger for coupling with the wire and for moving the wire with respect to the sheath; and a sheath control unit removably coupled to the wire actuation unit for independently controlling the position of the sheath, wherein the controller is configured to longitudinally move the wire and operate the basket device to selectively open and close the basket.

In accordance with another aspect, an example embodiment is provided in a tool for use by a surgeon, the tool for coupling to a leer port and for operating a sheath and wire including a basket device for capturing an object to be removed from a body of an animal, the tool comprising: a controller adapted to be coupled to the sheath and the wire for selectively controlling the position of the wire with respect to the sheath and for operating the basket device between a first, closed position and a second, open position, the controller comprising: a wire actuation unit comprising: a housing defining an axis, the housing including a passage having a first internal portion and a second external portion; and a plunger movable along the axis of the housing in the first internal passage, the plunger including a handle extending along the axis and outward from the housing, plunger for coupling with the wire and for moving the wire with respect to the sheath; and the second external portion of the housing of the wire actuation unit removably coupled sheath control unit.

In accordance with another aspect, an example method comprises operating a tool for use by a surgeon for capturing an object to be removed from a body of an animal, wherein the tool comprises a sheath and wire including an end including a basket device which may be opened when the end of the wire is moved external to an end of the sheath; a controller coupled to the sheath and wire for selectively controlling the position of the wire with respect to the sheath and for operating the basket device between a first, closed position and a second, open position, the controller including a base portion comprising a wire actuation unit including a movable plunger for coupling with the wire and for moving the wire with respect to the sheath; and a sheath control unit removably coupled to the wire actuation unit for independently controlling the position of the sheath; wherein the controller is configured to longitudinally move the wire and operate the basket device to selectively open and close the basket, the method of operation comprising the steps of: controlling the axial position of the basket device within the sheath by adjusting the axial position of the plunger within the controller; controlling the rotational position of the basket device by adjusting the rotational position of the plunger within the controller; and controlling the axial position of the sheath, when the tool is used with an endoscope and located in the body, by controlling the sheath control unit by a person other than the surgeon.

BRIEF DESCRIPTION OF THE DRAWINGS

The foregoing aspects and other features are explained in the following description, taken in connection with the accompanying drawings, wherein:

FIG. 7 is a cross sectional view of the plunger body of the controller shown in FIGS. 4-5;

FIG. 8 is a perspective view of the plunger of the controller shown in FIGS. 4-5;

DETAILED DESCRIPTION OF EMBODIMENTS

Figure 1:
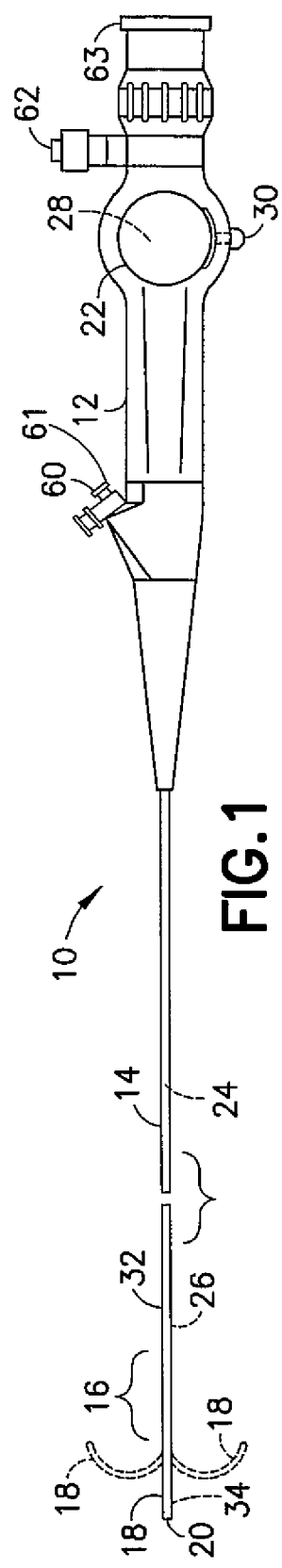
FIG. 1 is a side view of an endoscope.

Referring to FIG. 1, there is shown a side view of an example apparatus 10. The apparatus 10 in this example is an endoscope medical device configured to be partially inserted into a patient's body, such as in through the patient's urethra for example. The endoscope generally comprises a control section 12 and a flexible or semi-flexible shaft 14 connected to the control section 12. In this example the control section forms a handle for the apparatus. The shaft 14 includes a passive deflection section 16 and an active deflection section (bending section) 18 at the distal end of the shaft 14. A control system 22 to control the active deflection section 18 extends from the control section 12 to the active deflection section 18. The control system 22 generally comprises bending control wires, wire sheaths, and an actuator 28. The wires are connected to the actuator 28 at one end and are connected to the active deflection section 18 at a second end.

In the example embodiment shown, the control section 12 has a user operated slide or lever (control lever) 30. The lever 30 is connected to the actuator 28. The actuator 28 is adapted to pull and release the wires of the control system 22. When the lever 30 is moved by the user, the actuator 28 is moved. The actuator 28 may be, for example, a drum or pulley rotatably connected to the control section 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the control section will have additional actuators and corresponding controls to drive the additional pairs of bending control wires. In still other alternate embodiments, the control section may have knobs with rack and pinion mechanisms or other suitable user operated controls for the control system.

The shaft 14 is cantilevered from the control section 12. The flexible shaft 14 includes the bending control wires of the control system 22, a fiber optical image bundle, a fiber optical illumination bundle, and a working channel. A port 60 for inserting instruments into the working channel 24 of the shaft is located on the control section 12. The control section 12 also has a light source post 62 for connecting a light source (not shown) to the illumination bundle. In addition, the control section 12 has an eyepiece 63 for a user to view an image transmitted by the image bundle from the front end 20. In alternate embodiments, the flexible shaft may house different systems within. The shaft 14 generally comprises a frame 26, a cover 32 and an objective head 34.

Figure 2:
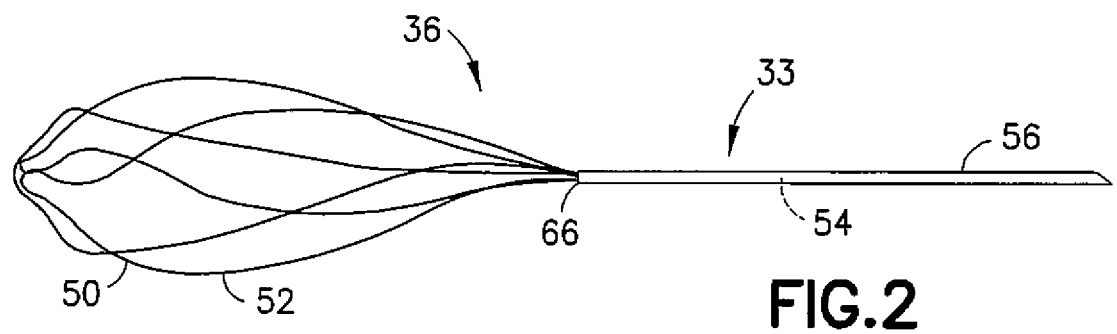
FIG. 2 is a side view of a distal end of an endoscopic tool.
Figure 3:
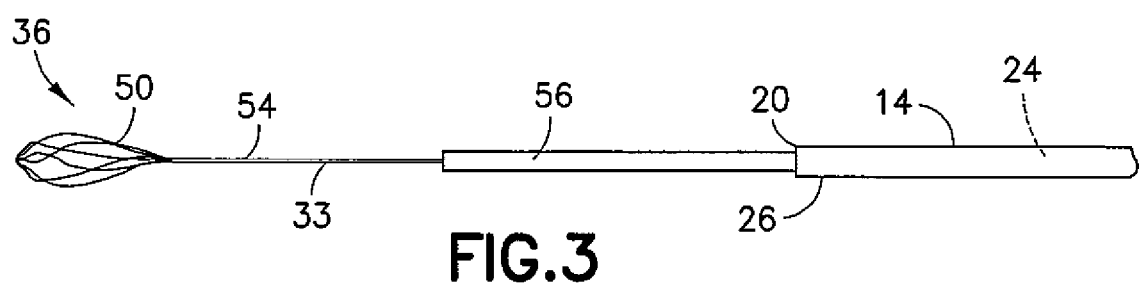
FIG. 3 is a side view illustrating extension of the tool shown in FIG. 2 from the distal end of the endoscope shown in FIG. 1.

Referring also to FIGS. 2-3, a distal end of an endoscopic tool 36 is shown. The tool 36 is configured to be attached to the apparatus 10 and is configured to extend out of the distal end 20 of the shaft 14 from the working channel 24. The tool 36, in this example, is a Surgeon Controlled Basket Device (SCBD). The tool 36 includes an assembly 33 which comprises a basket device and a sheath 56. The basket device 50 comprises a basket section 52 at a distal end, and a shaft section 54 extending through the sheath 56 to a proximal end of the tool 36. The shaft section 54 functions as a control wire for moving the basket section 52. The sheath 56 and basket device 50 are longitudinally movable relative to each other to move the basket device 50 between a forward position and a rearward position relative to the sheath 56. FIGS. 2 and 3 show the shaft section (control wire) 54 moved forward relative to the sheath 56 such that the basket section 52 is located out from a front end aperture 66 of the sheath 56. In the forward position of the sheath 56 on the basket device 50, the basket section 52 is located inside the sheath 56; the basket section 52 being collapsed by the sheath 56 into a smaller shape to fit inside the sheath 56.

Figure 4:
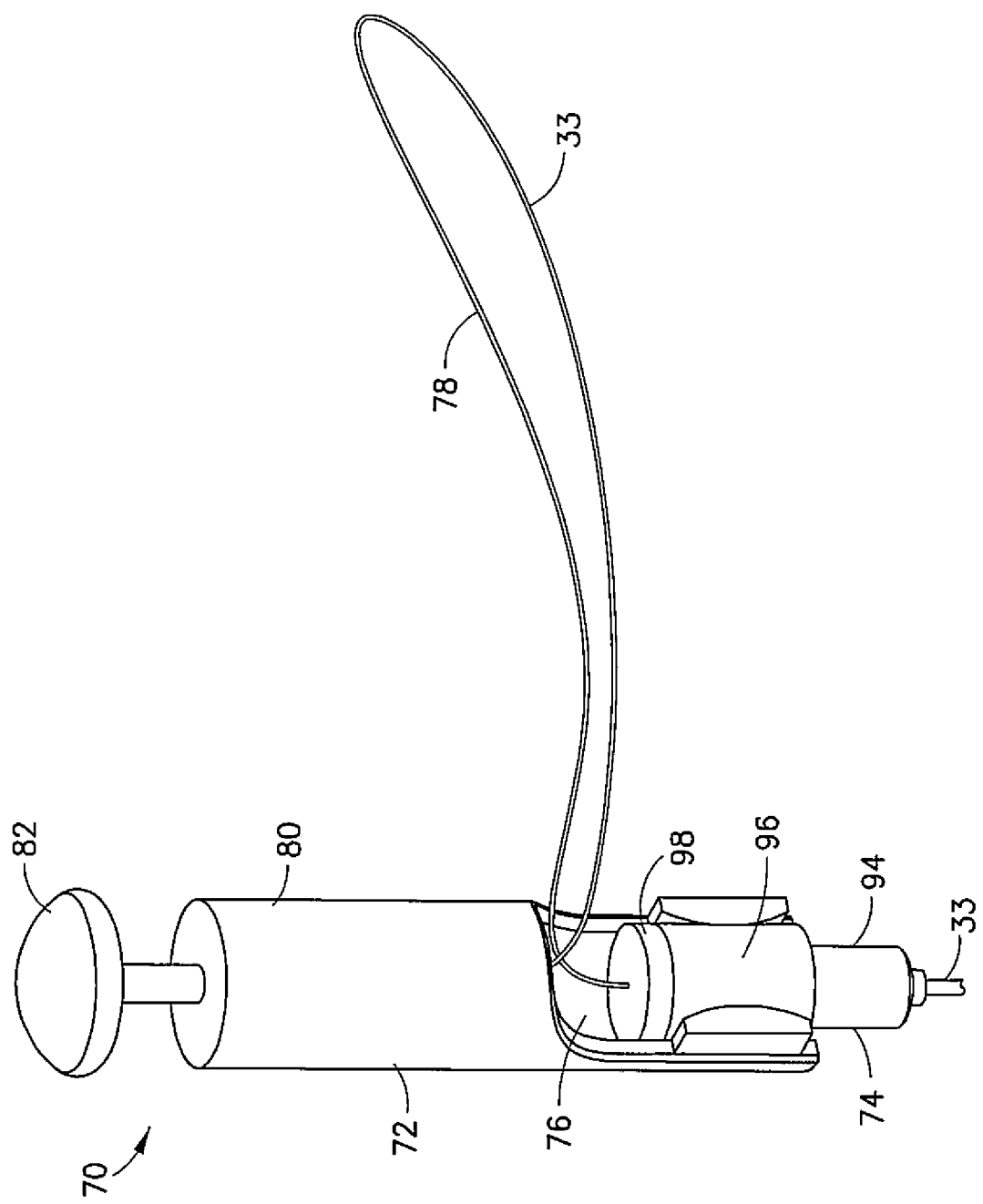
FIG. 4 is a perspective view of a proximal end of the endoscopic tool shown in FIGS. 2-3.
Figure 5:
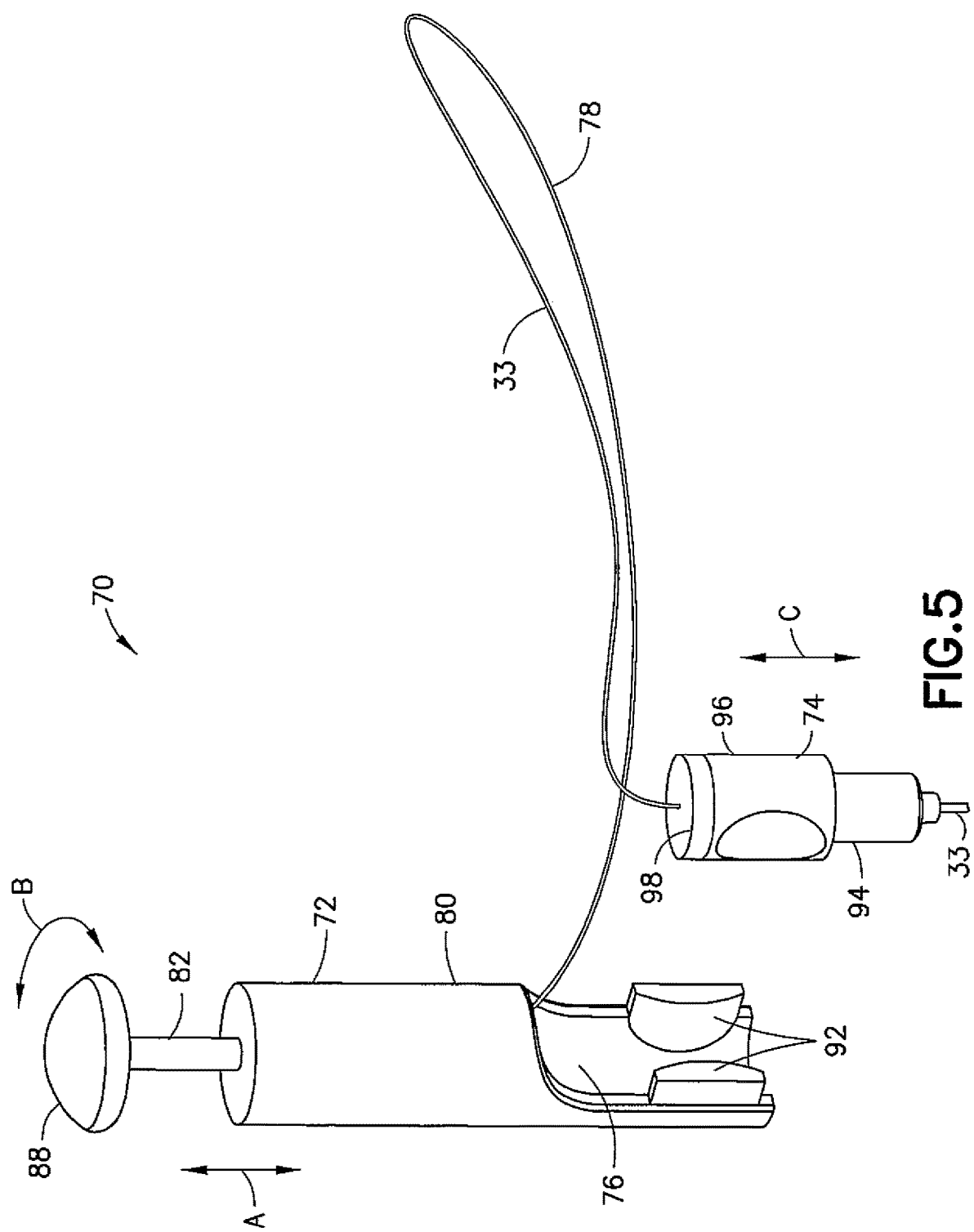
FIG. 5 is a perspective view of the proximal end of the endoscopic tool shown in FIG. 4 showing the first section of the controller disconnected from the second section of the controller.
Figure 9:
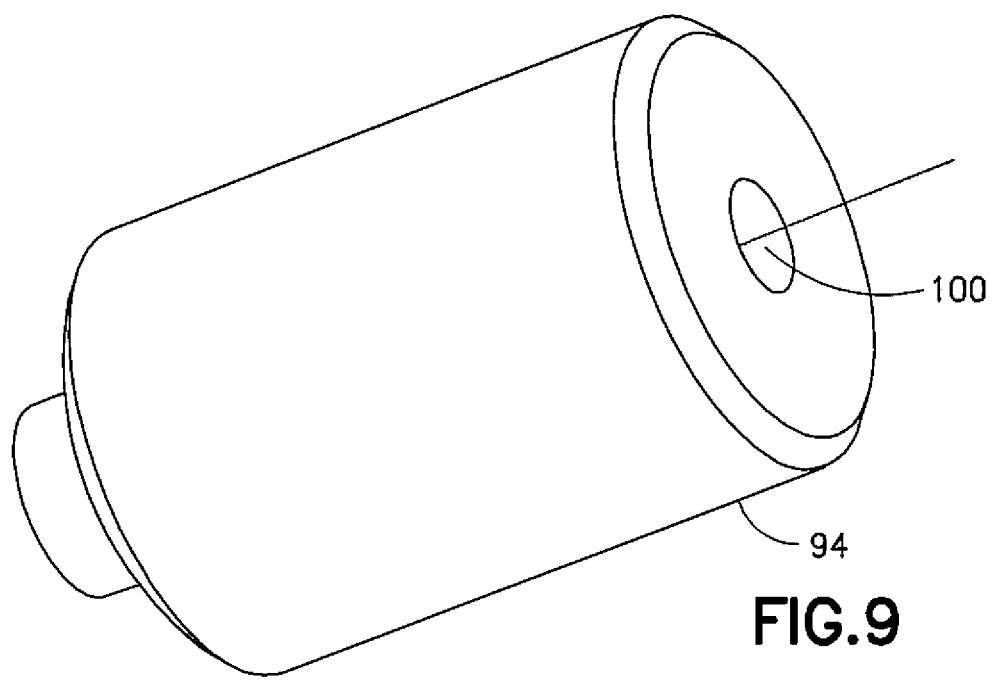
FIG. 9 is a perspective view of the connector of the controller shown in FIGS. 4-5.

Referring also to FIGS. 4-5, the proximal end of the tool 36 comprises a controller 70. The controller 70 generally comprises a first section 72 removably connected to a second section 74. The proximal end of the assembly 33 extends through the second section 74 and into the first section 72. In this example, when the first section 72 is connected to the second section 74 as seen in FIG. 4, a length of the assembly 33 extends out of an aperture 76 in the first section 72 in the form of a loop 78. As seen in comparing FIG. 4 to FIG. 5, the first section 72 may be removed from the second section 74, and the assembly 33 can still stay connected to both sections 72, 74. This allows the first section 72 to be disconnected from the endoscope 10 and operated at a spaced distance from the endoscope 10; perhaps by a different person than the person operating the endoscope 10.

Figure 6:
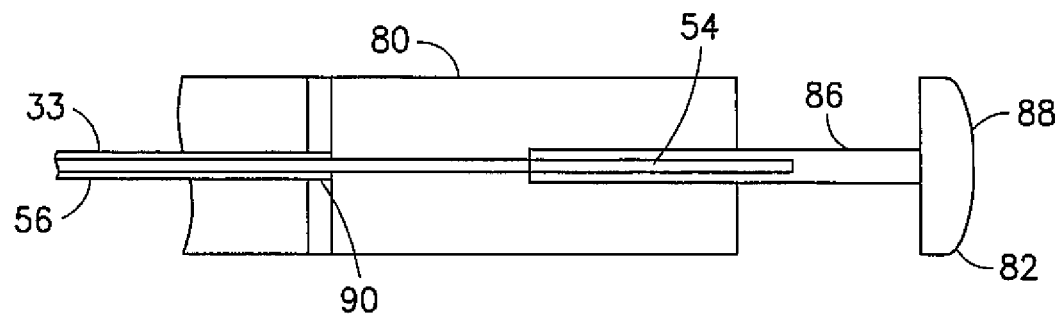
FIG. 6 is a schematic view illustrating connections of the sheath and basket device to the controller shown in FIGS. 4-5.

Referring also to FIGS. 6-8, the first section 72 generally comprises a plunger body 80 and a plunger 82. The plunger 82 is connected to the plunger body 80 and extends out of a top aperture 84 in the plunger body 80. The plunger 82 has a shaft 86 and a user contact section 88. As shown best in FIG. 5, the plunger 82 is connected to the plunger body 80 to be able to move on the plunger body linearly along the longitudinal axis of the plunger 82 as indicated by arrow A, and able to axially rotate on the plunger body as indicated by arrow B. The proximal end of the shaft section 54 of the basket device 50 is fixedly connected to the shaft 86 of the plunger 82 as schematically illustrated in FIG. 6. Thus, axial rotation of the plunger 82 axially rotates the basket device 50. Also, linear movement of the plunger 82 on the plunger body 80 results in axial linear movement of the basket device 50. The proximal end of the sheath 56 is fixedly connected to the plunger body 80 proximate the section 90 of the plunger body 80, and the proximal end of the sheath 56 is not directly connected to the plunger 82. Thus, longitudinal movement of the plunger 82 relative to the plunger body 80 as indicated by arrow A results in longitudinal movement of the basket device 50 relative to the sheath 56.

A spring (not shown) may be provided to bias the plunger 82 in a home extended position relative to the plunger body 80 as shown in FIGS. 4-5. The plunger 82 forms a basket actuation plunger which is able to move relative to the plunger body 80 to open and close the basket section 52. The basket deployment plunger 82 can also be axially rotated to rotate the basket section 52. A user may depress the plunger 82 into the plunger body 80 to thereby linearly move the basket device 50 relative to the sheath 56. This extends the basket section 52 out of the front end of the sheath 56 where the basket section 52 may expand due to its natural resilient properties and shape. The user may release the plunger 82 to allow the spring (not shown) to move the plunger 82 back towards its home extended position, thereby retracting the basket section 52 back towards the sheath 56 and capturing an object(s) in the collapsing basket section 52.

The bottom end of the plunger body 80 has opposing mounts 92. The mounts 92 are sized and shaped to allow the plunger body 80 to be laterally slid onto the second section 74 and thereby removably connect the first section 72 to the second section 74. The example embodiment of the first section 72 described above is merely exemplary. Components, features and operation could obviously be varied in other alternative example embodiments. Likewise, the connection of the first section 72 to the second section 74 could also be varied in regard to its components, features and operation, but still provide features as described herein.

Referring also to FIGS. 9-12, the second section generally comprises a connector 94, an advancement body 96 and a seal 98. The connector 94 is configured to removably mount onto the luer 61 at the port 60 of the endoscope 10. The luer 61 may extend into area 101 of the connector 94 and form a sealing compression friction fit thereat.

The advancement body 96 is movably mounted to the connector 94. In particular, the advancement body 96 is able to linearly move on the connector 94 as indicated by arrow C shown in FIG. 5 along the longitudinal axis of the second section 74. The advancement body 96 comprises exterior side recesses 102, shown in FIG. 11, and a connector receiving area 104, shown in FIG. 12, formed between the center tube section 106 and the outer wall 108. The recesses 102 are sized and shaped to removeably receive the mounts 92 of the first section 72 therein. This allows the first section 72 to be removably mounted to the second section 74.

Figure 10:
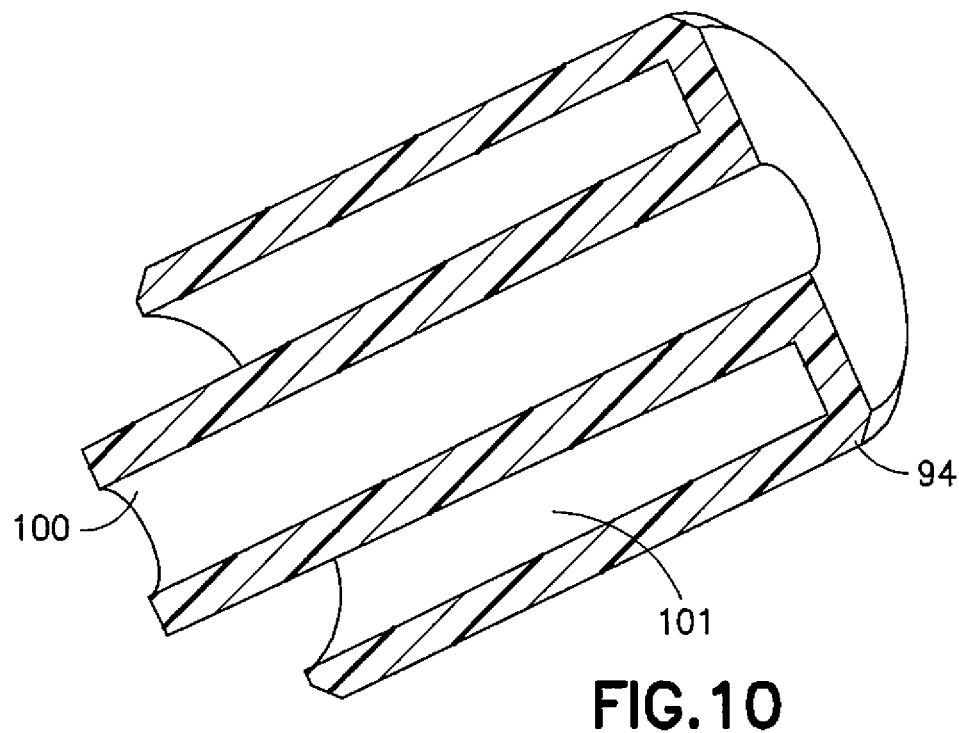
FIG. 10 is a cross sectional view of the connector shown in FIG. 9.
Figure 11:
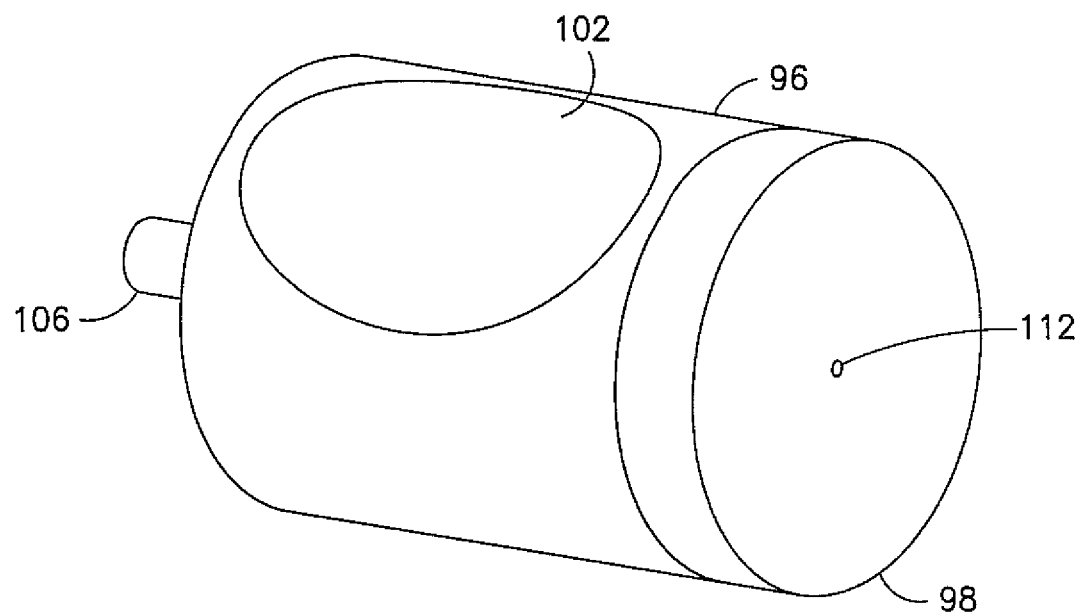
FIG. 11 is a perspective view of the advancement body of the controller shown in FIGS. 4-5.
Figure 12:
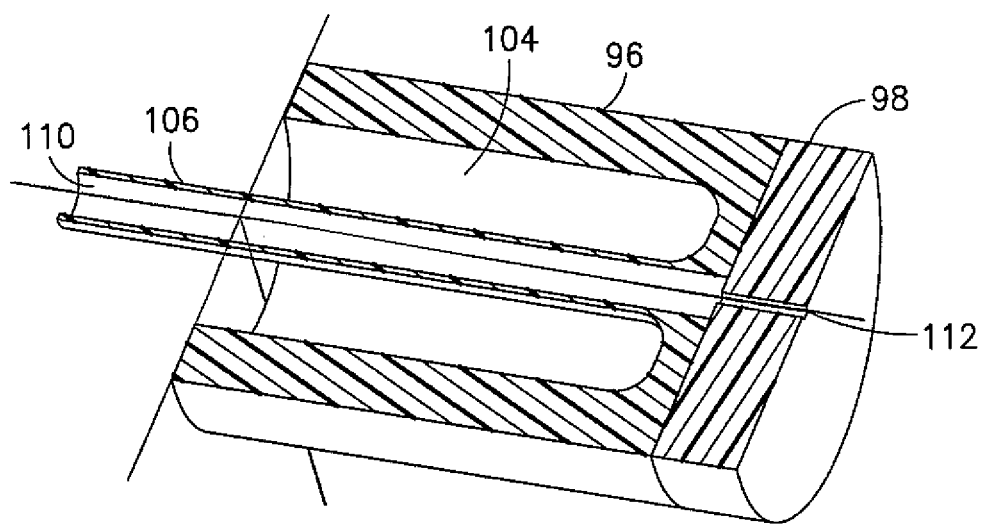
FIG. 12 is a cross sectional view of the advancement body shown in FIG. 11.

The center tube section 106, shown in FIGS. 11 and 12, is slidably located in the center channel 100, shown in FIG. 10, of the connector 94. The top half of the connector 94 is slidably located in the connector receiving area 104 of the advancement body 96. The center tube section 106 has a center channel 110 which the assembly 33 extends through. Located on the top side of the advancement body 96 is the seal 98 which is fixedly attached to the top side of the advancement body 96. The seal 98 has an aperture 112 which allows the assembly 33 to extend therethrough.

The sheath 56 is fixedly attached to the advancement body 96, such as by a compression friction fit at the seal 98 for example. Thus, when the advancement body 96 is linearly moved on the connector 94 as indicated by arrow C in FIG. 5, the sheath 56 is moved with the advancement body 96 and seal 98 relative to the connector 94 and the endoscope 10 (which the connector 94 is stationarily connected to). Because of the connection of the basket device 50 and the sheath 56 to the first section 72 of the controller 70, when the sheath 56 is moved by the second section 74 relative to the connector 94 and the endoscope 10, the basket device 50 is moved with the sheath 56. The advancement body 96 is able to move relative to Luer connection body 94 to move sheath and basket along the working channel 24. Movement of the advancement body 96 does not result in relative movement between the basket device 50 and the sheath 56. Instead, the second section 74 is designed to be able to function as a fine adjustment system for locating the distal end of the assembly 33 relative to the distal end of the endoscope. With this type of system, the user of the endoscope 10 can insert the tool 36 into the endoscope 10 and subsequently use the second section 74 to extend or retract the distal end of the assembly 33 to a desired target location relative to the front end of the endoscope without having to move the endoscope shaft 14. In an alternate example embodiment, this type of fine adjustment feature might not be provided. Alternatively, other types of designs could be used to provide this type of fine adjustment feature.

An example embodiment may be provided in a tool for use by a surgeon, the tool for coupling to a luer port or working channel port and for operating a sheath and wire including a basket device for capturing an object to be removed from a body of an animal, the tool comprising: a controller adapted to be coupled to the sheath and the wire for selectively controlling the position of the wire with respect to the sheath and for operating the basket device between a first, closed position and a second, open position, the controller including a base portion comprising: a wire actuation unit including a movable plunger for coupling with the wire and for moving the wire with respect to the sheath; and a sheath control unit removably coupled to the wire actuation unit for independently controlling the position of the sheath; wherein the controller is configured to longitudinally move the wire and operate the basket device to selectively open and close the basket.

The tool may further comprise a first biasing mechanism for biasing the basket device toward the first, closed position and wherein the sheath and wire includes a service portion located between the wire actuation unit and the sheath control unit for continued operation of the basket device when the wire actuation unit is removed from the sheath control unit. The sheath control unit may be separately controllable from the control of the wire actuation unit. The wire actuation unit, when uncoupled from the sheath control unit, may be controlled by a person other than the surgeon. The wire actuation unit may comprise: a housing defining an axis, the housing including a passage having a first internal portion and a second external portion; and a plunger movable along the axis of the housing in the passage, the plunger including an expanded distal region, the plunger extending along the axis and outward from the housing. The second exterior portion of the housing may be formed for grasping by the surgeon, wherein the handle of the plunger is adapted for the surgeon to push and release such that the controller can be operated with a single hand. The sheath control unit may be removably coupled to the second external portion of the passage of the housing of the wire actuation unit, the tool further comprising: a first biasing mechanism for biasing the plunger along the axis of the housing in a direction to move the basket device toward the first, closed position; wherein the sheath and wire includes a service portion located between the wire actuation unit and the sheath control unit for continued operation of the basket device when the sheath control unit is removed from the second external portion of the passage of the housing; and wherein the sheath control unit is provided with a seal. The axial position of the basket device may be controlled by adjusting the axial position of the plunger of the wire actuation unit. The rotational position of the basket device may be controlled by adjusting the rotational position of the plunger of the wire actuation unit. The axial position of the sheath, when used with an endoscope and located in the body, may be controlled by the sheath control unit and the wire actuation unit may be controlled by a person other than the surgeon. The axial position of the basket, when used with an endoscope and located in the body, may be controlled by the controller and may be controlled by a person other than the surgeon.

An example embodiment may be provided in a tool for use by a surgeon, the tool for coupling to a luer port and for operating a sheath and wire including a basket device for capturing an object to be removed from a body of an animal, the tool comprising: a controller adapted to be coupled to the sheath and the wire for selectively controlling the position of the wire with respect to the sheath and for operating the basket device between a first, closed position and a second, open position, the controller comprising: a wire actuation unit comprising: a housing defining an axis, the housing including a passage having a first internal portion and a second external portion; and a plunger movable along the axis of the housing in the first internal passage, the plunger including a handle extending along the axis and outward from the housing, plunger for coupling with the wire and a for moving the wire with respect to the sheath; and the second external portion of the housing of the wire actuation unit removably coupled sheath control unit.

The tool may further comprise a first biasing mechanism for biasing the plunger within the housing to bias the basket device toward the first, closed position; a sheath and wire assembly including a basket device; and wherein the sheath and wire assembly includes a service portion located between the wire actuation unit and the sheath control unit for continued operation of the basket device when the second external portion of the wire actuation unit is removed from the sheath control unit.

The sheath control unit may be separately controllable from the control of the wire actuation unit to control the position of the basket device. The wire actuation unit, when uncoupled from the sheath control unit, may be controlled by a person other than the surgeon.

An example method may be provided in a method of operating a tool for use by a surgeon for capturing an object to be removed from a body of an animal, wherein the tool comprises a sheath and wire including an end including a basket device which may be opened when the end of the wire is moved external to an end of the sheath; a controller coupled to the sheath and wire for selectively controlling the position of the wire with respect to the sheath and for operating the basket device between a first, closed position and a second, open position, the controller including a base portion comprising a wire actuation unit including a movable plunger for coupling with the wire and for moving the wire with respect to the sheath; and a sheath control unit removably coupled to the wire actuation unit for independently controlling the position of the sheath; wherein the controller is configured to longitudinally move the wire and operate the basket device to selectively open and close the basket, the method of operation comprising the steps of: controlling the axial position of the basket device within the sheath by adjusting the axial position of the plunger within the controller; controlling the rotational position of the basket device by adjusting the rotational position of the plunger within the controller; and controlling the axial position of the sheath, when the tool is used with an endoscope and located in the body, by controlling the sheath control unit by a person other than the surgeon.

The steps of controlling the axial position of the basket device and controlling the rotational position of the basket device may be controlled by the surgeon at the same time that the step of controlling the axial position of the sheath is controlled by a person other than the surgeon including the step of removing the sheath control unit from the wire actuation unit. The method may further comprise the step of the surgeon controlling an object breaking device while the person other than the surgeon controls the axial position of the sheath after the sheath control unit is removed from the wire actuation unit.

Features as described herein may be used in regard to a stone retrieval basket. Features as described herein may be used in regard to a handle which attaches to an endoscope. Features as described herein may be used in regard to surgeon control. Features as described herein may be used in regard to an adjustable seal. This may provide a plunger style, endoscope mounting, apparatus having a retrieval basket and, in particular, to an apparatus having a disengaging plunger style of stone retrieval basket handle.

In certain cases, it is better for a surgeon to pass a handle of a tool having a stone retrieval basket to an assistant so that the hands of the surgeon are free for other tasks. However, with a conventional tool having a stone retrieval basket that attaches directly to the luer port or working channel port of an endoscope, there is no allowance for this type of handing off a part of the control by the surgeon. In conventional tools, if the handle is removed from the forceps block at the luer port, then the sheath and wire of the tool having the stone retrieval basket are no longer long enough to reach the objective head of the endoscope.

In the example embodiment described above, the device contains a service loop for the sheath and wire and a split handle design. When the handle is split the sheath advancing functional unit remains on the forceps block and the basket actuating functional unit can be used from a distance equal to the length of the service loop. This allows the device to work while attached to the forceps block and when removed and handed to an assistant without retracting the sheath and wire into the working channel of the scope.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A tool for use by a surgeon, the tool for coupling to a working channel port and for operating a sheath and a wire including a basket device for capturing an object to be removed from a body of a human or an animal, the tool comprising:
   a controller adapted to be coupled to the sheath and the wire for selectively controlling a position of the wire with respect to the sheath and for operating the basket device between a first, closed position and a second, open position, the controller including a base portion comprising:
      a wire actuation unit including a housing defining an axis and a movable plunger for coupling with the wire and for moving the wire with respect to the sheath, the plunger movable along the axis of the housing; and
      a sheath control unit including an advancement body and a connector configured to removably mount onto the working channel port, the advancement body of the sheath control unit removably coupled to the housing of the wire actuation unit at a location along the axis of the housing, the advancement body of the sheath control unit movably mounted to the connector and fixedly attached to the sheath for independently controlling a position of the sheath;
   wherein the controller is configured to longitudinally move the wire and operate the basket device to selectively open and close the basket device.

2. The tool of claim 1 further comprising a first biasing mechanism for biasing the basket device toward the first, closed position, and wherein the sheath and the wire include a service portion located between the wire actuation unit and the sheath control unit for continued operation of the basket device when the wire actuation unit is removed from the sheath control unit.

3. The tool of claim 1 wherein the sheath control unit is configured to be separately controllable from control of the wire actuation unit.

4. The tool of claim 1 wherein the wire actuation unit, when uncoupled from the sheath control unit, is configured to be controlled by a person other than the surgeon.

5. The tool of claim 1 wherein the housing of the wire actuation unit includes a passage having a first internal portion and a second external portion, wherein the plunger includes an expanded distal region, and wherein the plunger extends along the axis and outward from the housing.

6. The tool of claim 5 wherein the second external portion of the housing is formed for grasping by the surgeon, wherein a handle of the plunger is adapted for the surgeon to push and release such that the controller is configured to be operated with a single hand.

7. The tool of claim 6 wherein the sheath control unit is removably coupled to the second external portion of the passage of the housing of the wire actuation unit, the tool further comprising:
a first biasing mechanism for biasing the plunger along the axis of the housing in a direction to move the basket device toward the first, closed position;
wherein the sheath and the wire include a service portion located between the wire actuation unit and the sheath control unit for continued operation of the basket device when the sheath control unit is removed from the second external portion of the passage of the housing; and
wherein the sheath control unit is provided with a seal.

8. The tool of claim 1 wherein an axial position of the basket device is controlled by adjusting an axial position of the plunger of the wire actuation unit.

9. The tool of claim 1 wherein a rotational position of the basket device is controlled by adjusting a rotational position of the plunger of the wire actuation unit.

10. The tool of claim 1 wherein an axial position of the sheath, when used with an endoscope and located in the body, is controlled by the sheath control unit and the wire actuation unit is configured to be controlled by a person other than the surgeon.

11. The tool of claim 1 wherein an axial position of the basket, when used with an endoscope and located in the body, is controlled by the controller and is configured to be controlled by a person other than the surgeon.

12. A tool for use by a surgeon, the tool for coupling to a working channel port for capturing an object to be removed from a body of a human or an animal, the tool comprising:
a sheath;
a wire including a basket device;
a controller adapted to be coupled to the sheath and the wire for selectively controlling a position of the wire with respect to the sheath and for operating the basket device between a first, closed position and a second, open position, the controller comprising:
a wire actuation unit comprising:
a housing defining an axis, the housing including a passage having a first internal portion and a second external portion; and
a plunger movable along the axis of the housing in the first internal portion, the plunger including a handle extending along the axis and outward from the housing, the plunger configured for coupling with the wire and for moving the wire with respect to the sheath; and
a sheath control unit removably coupled to the second external portion of the housing, the sheath control unit including an advancement body fixedly attached to the sheath and a connector configured to removably mount onto the working channel port, the advancement body movably mounted to the connector for independently controlling a position of the sheath.

13. The tool of claim 12 further comprising:
a first biasing mechanism for biasing the plunger within the housing to bias the basket device toward the first, closed position; and
a service portion located between the wire actuation unit and the sheath control unit for continued operation of the basket device when the second external portion of the wire actuation unit is removed from sheath control unit.

14. The tool of claim 12 wherein the sheath control unit is separately controllable from control of the wire actuation unit to control position of the basket device.

15. The tool of claim 12 wherein the wire actuation unit, when, uncoupled from the sheath control unit, is configured to be controlled by a person other than the surgeon.

16. A method of operating a tool for use by a surgeon for capturing an object to be removed from a body of an animal, wherein the tool comprises a sheath and wire including an end including a basket device which is configured to be opened when the end of the wire is moved external to an end of the sheath; a controller coupled to the sheath and wire for selectively controlling the position of the wire with respect to the sheath and for operating the basket device between a first, closed position and a second, open position, the controller including a base portion comprising: a wire actuation unit including a movable plunger for coupling with the wire and for moving the wire with respect to the sheath, the wire actuation unit further including a housing defining an axis, the plunger movable along the axis of the housing; and a sheath control unit including an advancement body and a connector removably mounted to a working channel port of an endoscope located in the body, the advancement body of the sheath control unit removably coupled to the housing of the wire actuation unit at a location along the axis of the housing, the advancement body of the sheath control unit movably mounted to the connector and fixedly attached to the sheath for independently controlling the position of the sheath; wherein the controller is configured to longitudinally move the wire and operate the basket device to selectively open and close the basket device, the method of operation comprising the steps of:
controlling the axial position of the basket device within the sheath by adjusting the axial position of the plunger within the controller;
controlling the rotational position of the basket device by adjusting the rotational position of the plunger within the controller; and
controlling the axial position of the sheath by controlling the sheath control unit by a person other than the surgeon.

17. The method of operating the tool of claim 16 wherein the steps of controlling the axial position of the basket device and controlling the rotational position of the basket device are controlled by the surgeon at the same time that the step of controlling the axial position of the sheath is controlled by a person other than the surgeon including the step of removing the sheath control unit from the wire actuation unit.

18. The method of operating the tool of claim 16 further comprising the step of the surgeon controlling an object breaking device while the person other than the surgeon controls the axial position of the sheath after the sheath control unit is removed from the wire actuation unit.

* * * * *